(12) United States Patent
Mitsuhashi et al.

(10) Patent No.: US 10,450,413 B2
(45) Date of Patent: Oct. 22, 2019

(54) SILANE COMPOUND CONTAINING PERFLUORO(POLY)ETHER GROUP

(71) Applicant: DAIKIN INDUSTRIES, LTD., Osaka-shi, Osaka (JP)

(72) Inventors: Hisashi Mitsuhashi, Osaka (JP); Mayuko Takano, Osaka (JP); Takashi Namikawa, Osaka (JP); Takashi Nomura, Osaka (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 0 days.

(21) Appl. No.: 15/748,986

(22) PCT Filed: Jul. 13, 2016

(86) PCT No.: PCT/JP2016/070721
§ 371 (c)(1),
(2) Date: Jan. 30, 2018

(87) PCT Pub. No.: WO2017/022437
PCT Pub. Date: Feb. 9, 2017

(65) Prior Publication Data
US 2019/0002635 A1   Jan. 3, 2019

(30) Foreign Application Priority Data

Jul. 31, 2015 (JP) ................. 2015-152468
Sep. 14, 2015 (JP) ................. 2015-181146
Oct. 30, 2015 (JP) ................. 2015-215019

(51) Int. Cl.
| | |
|---|---|
| *C09D 5/16* | (2006.01) |
| *C09D 171/02* | (2006.01) |
| *C07F 7/18* | (2006.01) |
| *C09K 3/18* | (2006.01) |
| *C08G 65/336* | (2006.01) |

(52) U.S. Cl.
CPC .............. *C08G 65/336* (2013.01); *C07F 7/18* (2013.01); *C09D 5/16* (2013.01); *C09D 171/02* (2013.01); *C09K 3/18* (2013.01)

(58) Field of Classification Search
CPC .................. C07F 7/18; C08G 65/336
See application file for complete search history.

(56) References Cited

U.S. PATENT DOCUMENTS

| | | |
|---|---|---|
| 6,183,872 B1 | 2/2001 | Tanaka et al. |
| 2009/0208728 A1 | 8/2009 | Itami et al. |
| 2010/0324253 A1 | 12/2010 | Ito |
| 2015/0118502 A1 | 4/2015 | Mitsuhashi et al. |
| 2015/0118504 A1 | 4/2015 | Ohshita et al. |
| 2016/0304665 A1 | 10/2016 | Sakoh et al. |
| 2016/0340544 A1 | 11/2016 | Katsukawa et al. |

FOREIGN PATENT DOCUMENTS

| | | |
|---|---|---|
| EP | 3085749 A1 | 10/2016 |
| JP | 2006-113134 A | 4/2006 |
| JP | 2008-534696 A | 8/2008 |
| JP | 2009-191101 A | 8/2009 |
| JP | 2014-144935 A | 8/2014 |
| JP | 2016-204656 A | 12/2016 |
| WO | 97/07155 A1 | 2/1997 |
| WO | 2009/101986 A1 | 8/2009 |
| WO | 2011/059430 A1 | 5/2011 |
| WO | 2013/146110 A1 | 10/2013 |
| WO | 2013/187432 A1 | 12/2013 |
| WO | 2015/099085 A1 | 7/2015 |

OTHER PUBLICATIONS

International Preliminary Report on Patentability with a Translation of Written Opinion issued from the International Bureau in counterpart International Application No. PCT/JP2016/070721, dated Feb. 15, 2018.
International Search Report for PCT/JP2016/070721 dated Oct. 4, 2016 [PCT/ISA/210].
Communication dated Jul. 2, 2018 from the European Patent Office in counterpart European application No. 16832716.1.
Communication dated Apr. 4, 2019 from the European Patent Office in application No. 16832716.1.

*Primary Examiner* — Ramsey Zacharia
(74) *Attorney, Agent, or Firm* — Sughrue Mion, PLLC

(57) ABSTRACT

The present invention provides a perfluoro(poly)ether group containing silane compound of $$(Rf\text{-}PFPE)_\beta\text{-}X\text{—}(CR^a_k R^b_l R^c_m)_\alpha \qquad (1a)$$

$$(R^c_m R^b_l R^a_k C)_\alpha\text{—}X\text{-}PFPE\text{-}X\text{—}(CR^a_k R^b_l R^c_m)_\alpha \qquad (1b)$$

wherein the symbols are as defined in the description.

23 Claims, No Drawings

SILANE COMPOUND CONTAINING PERFLUORO(POLY)ETHER GROUP

CROSS REFERENCE TO RELATED APPLICATIONS

This application is a National Stage of International Application No. PCT/JP2016/070721 filed Jul. 13, 2016, claiming priority based on Japanese Patent Application Nos. 2015-152468 filed Jul. 31, 2015; 2015-181146 filed Sep. 14, 2015 and 2015-215019 filed Oct. 30, 2015, the contents of all of which are incorporated herein by reference in their entirety.

TECHNICAL FIELD

The present invention relates to a perfluoro(poly)ether group containing silane compound.

BACKGROUND ART

A certain fluorine-containing silane compound is known to be able to provide excellent water-repellency, oil-repellency, antifouling property, or the like when it is used in a surface treatment of a base material. A layer (hereinafter, referred to as a "surface-treating layer") formed from a surface-treating agent comprising a fluorine-containing silane compound is applied to various base materials such as a glass, a plastic, a fiber and a building material as a so-called functional thin film.

As such fluorine-containing compound, a perfluoropolyether group containing silane compound which has a perfluoropolyether group in its main molecular chain and a hydrolyzable group bonding to a Si atom in its molecular terminal or terminal portion is known (Patent Documents 1 and 2).

PRIOR ART DOCUMENT

Patent Document

Patent Document 1: JP 2008-534696 A
Patent Document 2: International Publication No. 97/07155

SUMMARY OF THE INVENTION

Problem to be Solved by the Invention

The surface-treating layer is requested for high durability to provide a base material with a desired function for a long time. The layer formed from the surface-treating agent containing the perfluoropolyether group containing silane compound has been suitably used in an optical member such as glasses, a touch panel or the like which is required to have light permeability or transparency since it can exert the above functions even in form of a thin film. In particular, in these applications, the friction durability is required to be further improved.

However, a layer formed from a surface-treating agent containing a conventional perfluoropolyether group containing silane compound described above is no longer necessarily enough to meet the increasing demand to improve the friction durability.

An object of the present invention is to provide a perfluoro(poly)ether group containing silane compound which is able to form a layer having water-repellency, oil-repellency and antifouling property as well as high friction durability.

Means to Solve the Problem

As a result of intensively studying, the inventors of the present invention have found that use of a perfluoropolyether group containing silane compound having a plurality of Si atom having a hydrolyzable group improves friction durability, and the inventors reach the present invention.

According to the first aspect of the present invention, there is provided a perfluoro(poly)ether group containing silane compound of formula (1a) or formula (1b):

(1a)

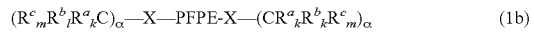
(1b)

wherein:
Rf is each independently at each occurrence an alkyl group having 1-16 carbon atoms which may be substituted by one or more fluorine atoms;
PFPE is each independently at each occurrence a group of the formula:

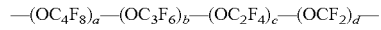

wherein a, b, c and d are each independently an integer of 0-200, the sum of a, b, c and d is 1 or more, and the occurrence order of the respective repeating units in parentheses with the subscript a, b, c or d is not limited in the formula;
X is each independently a single bond or a 2-10 valent organic group;
$\alpha$ is each independently an integer of 1-9;
$\beta$ is an integer of 1-9;
$R^a$ is each independently at each occurrence $-Z-CR^1_pR^2_qR^3_r$;
Z is each independently at each occurrence an oxygen atom or a divalent organic group;
$R^1$ is each independently at each occurrence $R^{a\prime}$;
$R^{a\prime}$ has the same definition as that of $R^a$;
in $R^a$, the number of C atoms which are straightly linked via the Z group is up to five;
$R^2$ is each independently at each occurrence $-Y-SiR^5_nR^6_{3-n}$;
Y is each independently at each occurrence an oxygen atom or a divalent organic group;
$R^5$ is each independently at each occurrence a hydroxyl group or a hydrolyzable group;
$R^6$ is each independently at each occurrence a hydrogen atom or a lower alkyl group;
n is an integer of 1-3 independently per unit $-Y-SiR^5_nR^6_{3-n}$;
$R^3$ is each independently at each occurrence a hydrogen atom or a lower alkyl group;
p is each independently at each occurrence an integer of 0-3;
q is each independently at each occurrence an integer of 0-3;
r is each independently at each occurrence an integer of 0-3;
$R^b$ is each independently at each occurrence $-Y-SiR^5_nR^6_{3-n}$;
$R^c$ is each independently at each occurrence a hydrogen atom or a lower alkyl group;
k is each independently at each occurrence an integer of 0-3;

l is each independently at each occurrence an integer of 0-3; and m is each independently at each occurrence an integer of 0-3;

with the proviso that in the formula at least one q is 2 or 3, or at least one l is 2 or 3.

According to the second aspect of the present invention, there is provided a surface-treating agent comprising the perfluoro(poly)ether group containing silane compound described above.

According to the third aspect of the present invention, there is provided a pellet comprising the surface-treating agent described above.

According to the fourth aspect of the present invention, there is provided an article comprising a base material and a layer which is formed on a surface of the base material from the perfluoro(poly)ether group containing silane compound described above or the surface-treating agent described above.

Effect of the Invention

According to the present invention, there is provided a novel perfluoro(poly)ether group containing silane compound. Furthermore, there is provided a surface treating agent obtained by using the perfluoro(poly)ether group containing silane compound. By using them, the surface-treating layer having water-repellency, oil-repellency and antifouling property as well as excellent friction durability can be formed.

EMBODIMENTS TO CARRY OUT THE INVENTION

Hereinafter, the compound of the present invention will be described.

A "hydrocarbon group" as used herein represents a group containing a carbon atom and a hydrogen atom which is obtained by removing a hydrogen atom from a hydrocarbon. Examples of the hydrocarbon group include, but are not particularly limited to, a hydrocarbon group having 1-20 carbon atoms which may be substituted with one or more substituents, for example, an aliphatic hydrocarbon group, an aromatic hydrocarbon group, and the like. The "aliphatic hydrocarbon group" may be straight, branched or cyclic, and may be saturated or unsaturated. The hydrocarbon group may contain one or more ring structures. It is noted that the hydrocarbon group may have one or more N, O, S, Si, amide, sulfonyl, siloxane, carbonyl, carbonyloxy, or the like at its end or in its molecular chain.

As used herein, examples of the substituent of the "hydrocarbon group" include, but are not particularly limited to, for example a halogen atom; and a $C_{1-6}$ alkyl group, a $C_{2-6}$ alkenyl group, a $C_{2-6}$ alkynyl group, a $C_{3-10}$ cycloalkyl group, a $C_{3-10}$ unsaturated cycloalkyl group, a 5-10 membered heterocyclyl group, a 5-10 membered unsaturated heterocyclyl group, a $C_{6-10}$ aryl group, a 5-10 membered heteroaryl group, and the like, which may be substituted by one or more halogen atoms.

As used herein, an "organic group" represents a group containing a carbon atom. A "2-10 valent organic group" represents a 2-10 valent group containing a carbon atom. Examples of the 2-10 valent organic group include, but are not particularly limited to, a 2-10 valent group obtained by removing 1-9 hydrogen atoms from a hydrocarbon group. For example, examples of the divalent organic group include, but are not particularly limited to, a divalent group obtained by removing one hydrogen atom from a hydrocarbon group from a hydrocarbon group.

The present invention provides a perfluoro(poly)ether group (hereinafter, also referred to as "PFPE") containing silane compound of the formula (1a) or the formula (1b) (hereinafter, also referred to as "a PFPE containing silane compound of the present invention").

(1a)

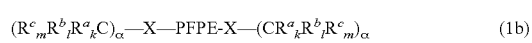

(1b)

In the formula, Rf is an alkyl group having 1-16 carbon atoms which may be substituted by one or more fluorine atoms.

The "alkyl group having 1-16 carbon atoms" in the alkyl having 1-16 carbon atoms which may be substituted by one or more fluorine atoms may be straight or branched, and preferably is a straight or branched alkyl group having 1-6 carbon atoms, in particular 1-3 carbon atoms, more preferably a straight alkyl group having 1-3 carbon atoms.

Rf is preferably an alkyl having 1-16 carbon atoms substituted by one or more fluorine atoms, more preferably a $CF_2H$—$C_{1-15}$ fluoroalkylene group, more preferably a perfluoroalkyl group having 1-16 carbon atoms.

The perfluoroalkyl group having 1-16 carbon atoms may be straight or branched, and preferably is a straight or branched perfluoroalkyl group having 1-6 carbon atoms, in particular 1-3 carbon atoms, more preferably a straight perfluoroalkyl group having 1-3 carbon atoms, specifically —$CF_3$, —$CF_2CF_3$ or —$CF_2CF_2CF_3$.

In the formula described above, PFPE is —$(OC_4F_8)_a$—$(OC_3F_6)_b$—$(OC_2F_4)_c$—$(OCF_2)_d$—, and corresponds to a perfluoro(poly)ether group. Herein, a, b, c and d are each independently 0 or an integer of 1 or more. The sum of a, b, c and d is 1 or more. Preferably, a, b, c and d are each independently an integer of 0 or more and 200 or less, for example an integer of 1 or more and 200 or less, more preferably each independently an integer of 0 or more and 100 or less, for example an integer of 1-200. The sum of a, b, c and d is preferably 5 or more, more preferably 10 or more, for example 10 or more and 100 or less. The occurrence order of the respective repeating units in parentheses with the subscript a, b, c or d is not limited in the formula. Among these repeating units, the —$(OC_4F_8)$—group may be any of —$(OCF_2CF_2CF_2CF_2)$—, —$(OCF(CF_3)CF_2CF_2)$—, —$(OCF_2CF(CF_3)CF_2)$—, —$(OCF_2CF_2CF(CF_3))$—, —$(OC(CF_3)_2CF_2)$—, —$(OCF_2C(CF_3)_2)$—, —$(OCF(CF_3)CF(CF_3))$—, —$(OCF(C_2F_5)CF_2)$— and —$(OCF_2CF(C_2F_5))$—, preferably —$(OCF_2CF_2CF_2CF_2)$—. The —$(OC_3F_6)$—group may be any of —$(OCF_2CF_2CF_2)$—, —$(OCF(CF_3)CF_2)$— and —$(OCF_2CF(CF_3))$—, preferably —$(OCF_2CF_2CF_2)$—. The —$(OC_2F_4)$—group may be any of —$(OCF_2CF_2)$— and —$(OCF(CF_3))$—, preferably —$(OCF_2CF_2)$—.

In one embodiment, PFPE is —$(OC_3F_6)_b$— wherein b is an integer of 1 or more and 200 or less, preferably 5 or more and 200 or less, more preferably 10 or more and 200 or less, preferably —$(OCF_2CF_2CF_2)_b$— wherein b is an integer of 1 or more and 200 or less, preferably 5 or more and 200 or less, more preferably 10 or more and 200 or less, or —$(OCF(CF_3)CF_2)_b$— wherein b is an integer of 1 or more and 200 or less, preferably 5 or more and 200 or less, more preferably 10 or more and 200 or less, more preferably —$(OCF_2CF_2CF_2)_b$— wherein b is an integer of 1 or more and 200 or less, preferably 5 or more and 200 or less, more preferably 10 or more and 200 or less.

In another embodiment, PFPE is —$(OC_4F_8)_a$—$(OC_3F_6)_b$—$(OC_2F_4)_c$—$(OCF_2)_d$— wherein a and b are each independently an integer of 0 or more and 30 or less, c and d are each independently an integer of 1 or more and 200 or less, preferably 5 or more and 200 or less, more preferably 10 or more and 200 or less, and the occurrence order of the respective repeating units in parentheses with the subscript a, b, c or d is not limited in the formula; preferably —$(OCF_2CF_2CF_2CF_2)_a$—$(OCF_2CF_2CF_2)_b$—$(OCF_2CF_2)_c$—$(OCF_2)_d$—. In one embodiment, PFPE may be —$(OC_2F_4)_c$—$(OCF_2)_d$— wherein c and d are each independently an integer of 1 or more and 200 or less, preferably 5 or more and 200 or less, more preferably 10 or more and 200 or less, and the occurrence order of the respective repeating units in parentheses with the subscript c or d is not limited in the formula.

In one embodiment, In —$(OC_4F_8)_a$—$(OC_3F_6)_b$—$(OC_2F_4)_c$—$(OCF_2)_d$— described above, a lower limit of a ratio of c to d (hereinafter, referred to as an "c/d ratio") may be 0.2, preferably 0.3, and an upper limit of the c/d ratio may be 1.5, preferably 1.3, more preferably 1.1, further preferably 0.9. By setting the c/d ratio to less than 1.5, slip property and friction durability of the surface-treating layer formed from the compound are more increased. The lower the c/d ratio, the higher the slip property and the higher the friction durability of the surface-treating layer becomes. Additionally, by setting the c/d ratio to 0.2 or more, stability of the compound can be more increased. The higher the c/d ratio, the higher the stability of the compound becomes.

In further another embodiment, PFPE is a group of —$(OC_2F_4$—$R^8)_{n''}$—. In the formula, $R^8$ is a group selected from $OC_2F_4$, $OC_3F_6$ and $OC_4F_8$, or a combination of 2 or 3 groups independently selected from these groups. Examples of the combination of 2 or 3 groups independently selected from $OC_2F_4$, $OC_3F_6$ and $OC_4F_8$ include, but not limited to, for example, —$OC_2F_4OC_3F_6$—, —$OC_2F_4OC_4F_e$—, —$OC_3F_6OC_2F_4$—, —$OC_3F_6OC_3F_6$—, —$OC_3F_6OC_4F_8$—, —$OC_4F_8OC_4F_8$—, —$OC_4F_8OC_3F_6$—, —$OC_4F_8OC_2F_4$—, —$OC_2F_4OC_2F_4OC_3F_6$—, —$OC_2F_4OC_2F_4OC_4F_8$—, —$OC_2F_4OC_3F_6OC_2F_4$—, —$OC_2F_4OC_3F_6OC_3F_6$—, —$OC_2F_4OC_4F_8OC_2F_4$—, —$OC_3F_6OC_2F_4OC_2F_4$—, —$OC_3F_6OC_2F_4OC_3F_6$—, —$OC_3F_6OC_3F_6OC_2F_4$—, —$OC_4F_8OC_2F_4OC_2F_4$—, and the like. n" is an integer of 2-100, preferably an integer of 2-50. In the above-mentioned formula, $OC_2F_4$, $OC_3F_6$ and $OC_4F_8$ may be straight or branched, preferably straight. In this embodiment, PFPE is preferably —$(OC_2F_4$—$OC_3F_6)_{n''}$— or —$(OC_2F_4$—$OC_4F_8)_f$—.

In the formula, X is each independently a single bond or a 2-10 valent organic group. X is recognized to be a linker which connects between a perfluoropolyether moiety (i.e., an Rf-PFPE moiety or -PFPE- moiety) providing mainly water-repellency, surface slip property and the like and a moiety (i.e., a group in parentheses with the subscript α) providing an ability to bind to a base material in the compound of the formula (1a) and (1b). Therefore, X may be any organic group as long as the compound of the formula (1a) and (1b) can stably exist.

In the formula, α is an integer of 1-9, and β is an integer of 1-9. α and β may be varied depending on the valence number of the X group. In the formula (1a), the sum of α and β is the valence number of X. For example, when X is a 10 valent organic group, the sum of α and β is 10, for example, α is 9 and β is 1, α is 5 and β is 5, or α is 1 and β is 9. When X is a divalent organic group, α and β are 1. In the formula (1b), α is a value obtained by subtracting 1 from the valence number of X.

X is preferably a 2-7 valent, more preferably 2-4 valent, more preferably a divalent organic group.

In one embodiment, X is a 2-4 valent organic group, α is 1-3, and β is 1.

In another embodiment, X is a divalent organic group, α is 1, and β is 1. In this case, the formulae (1a) and (1b) are represented by the following formulae (1a') and (1b').

$$\text{Rf-PFPE-X—CR}^a_k R^b_l R^c_m \quad (1a')$$

$$R^c_m R^b_l R^a_k C\text{—X—PFPE-X—CR}^a_k R^b_l R^c_m \quad (1b')$$

Examples of X include, but are not particularly limited to, for example a divalent group of the following formula:

$$—(R^{31})_{p'}—(X^a)_{q'}—$$

wherein:
$R^{31}$ is each independently a single bond, —$(CH_2)_{s'}$— or an o-, m- or p-phenylene group, preferably —$(CH_2)_{s'}$—,
s' is an integer of 1-20, preferably an integer of 1-6, more preferably an integer of 1-3, further more preferably 1 or 2,
$X^a$ is —$(X^b)_{l'}$—,
$X^b$ is each independently at each occurrence a group selected from the group consisting of —O—, —S—, an o-, m- or p-phenylene group, —C(O)O—, —Si($R^{33}$)$_2$—, —(Si($R^{33}$)$_2$O)$_{m'}$—Si($R^{33}$)$_2$—, —CONR$^{34}$—, —O—CONR$^{34}$—, —NR$^{34}$— and —$(CH_2)_{n'}$—,
$R^{33}$ is each independently at each occurrence a phenyl group, a $C_{1-6}$ alkyl group or a $C_{1-6}$ alkoxy group, preferably a phenyl group or a $C_{1-6}$ alkyl group, more preferably a methyl group,
$R^{34}$ is each independently at each occurrence a hydrogen atom, a phenyl group or a $C_{1-6}$ alkyl group (preferably a methyl group),
m' is each independently at each occurrence an integer of 1-100, preferably an integer of 1-20,
n' is each independently at each occurrence an integer of 1-20, preferably an integer of 1-6, more preferably an integer of 1-3,
l' is an integer of 1-10, preferably an integer of 1-5, more preferably an integer of 1-3,
p' is 0 or 1,
q' is 0 or 1, and
at least one of p' and q' is 1, and the occurrence order of the respective repeating units in parentheses with the subscript p' or q' is not limited in the formula. Here, $R^{31}$ and $X^a$ (typically, a hydrogen atom in $R^{31}$ and $X^a$) may be substituted with one or more substituents selected from a fluorine atom, a $C_{1-3}$ alkyl group and a $C_{1-3}$ fluoroalkyl group.

Preferably, X is
a $C_{1-20}$ alkylene group,
—$R^{31}$—$X^c$—$R^{31}$—, or
—$X^d$—$R^{31}$—
wherein $R^{31}$ is as defined above.

More preferably, X is
an $C_{1-20}$ alkylene group,
—$(CH_2)_{s'}$—$X^c$—,
—$(CH_2)_{s'}$—$X^c$—$(CH_2)_{t'}$—
—$X^d$—, or
—$X^d$—$(CH_2)_{t'}$—
wherein s' and t' are as defined above.

In the formula, $X^c$ is
—O—,
—S—,
—C(O)O—,
—CONR$^{34}$—,
—O—CONR$^{34}$—,
—Si($R^{33}$)$_2$—, —(Si($R^{33}$)$_2$O)$_{m'}$—Si($R^{33}$)$_2$—,
—O—(CH$_2$)$_{u'}$—(Si($R^{33}$)$_2$O)$_{m'}$—Si($R^{33}$)$_2$—,
—O—(CH$_2$)$_{u'}$—Si($R^{33}$)$_2$—O—Si($R^{33}$)$_2$—CH$_2$CH$_2$—Si($R^{33}$)$_2$—O—Si($R^{33}$)$_2$—,
—O—(CH$_2$)$_{u'}$—Si(OCH$_3$)$_2$OSi(OCH$_3$)$_2$—,
—CONR$^{34}$—(CH$_2$)$_{u'}$—(Si($R^{33}$)$_2$O)$_{m'}$—Si($R^{33}$)$_2$—,
—CONR$^{34}$—(CH$_2$)$_{u'}$—N($R^{34}$)—, or
—CONR$^{34}$-(o-, m- or p-phenylene)-Si($R^{33}$)$_2$—,
wherein $R^{33}$, $R^{34}$ and m' are as defined above, and
u' is an integer of 1-20, preferably an integer of 2-6, more preferably an integer of 2-3. $X^c$ is preferably —O—.

In the formula, $X^d$ is
—S—,
—C(O)O—,
—CONR$^{34}$—,
—CONR$^{34}$—(CH$_2$)$_{u'}$—(Si($R^{33}$)$_2$O)$_{m'}$—Si($R^{33}$)$_2$—,
—CONR$^{34}$—(CH$_2$)$_{u'}$—N($R^{34}$)—, or
—CONR$^{34}$-(o-, m- or p-phenylene)-Si($R^{33}$)$_2$—
wherein each of symbols is as defined above.

More preferably, X is
an $C_{1-20}$ alkylene group,
—(CH$_2$)$_{s'}$—$X^c$—(CH$_2$)$_{t'}$—, or
—$X^d$—(CH$_2$)$_{t'}$—
wherein each of symbols is as defined above.

Further more preferably, X is
an $C_{1-20}$ alkylene group,
—(CH$_2$)$_{s'}$—O—(CH$_2$)$_{t'}$—,
—(CH$_2$)$_{s'}$—(Si($R^{33}$)$_2$O)$_{m'}$—Si($R^{33}$)$_2$—(CH$_2$)$_{t'}$—,
—(CH$_2$)$_{s'}$—O—(CH$_2$)$_{u'}$—(Si($R^{33}$)$_2$O)$_{m'}$—Si($R^{33}$)$_2$—(CH$_2$)$_{t'}$—, or
—(CH$_2$)$_{s'}$—O—(CH$_2$)$_{t'}$—Si($R^{33}$)$_2$—(CH$_2$)$_{u'}$—Si($R^{33}$)$_2$—(C$_v$H$_{2v}$)—
wherein $R^{33}$, m', s', t' and u' are as defined above, and v is an integer of 1-20, preferably an integer of 2-6, more preferably an integer of 2-3.

In the formula, —(C$_v$H$_{2v}$)— may be straight or branched, for example, may be, for example, —CH$_2$CH$_2$—, —CH$_2$CH$_2$CH$_2$—, —CH(CH$_3$)—, —CH(CH$_3$)CH$_2$—.

X may be substituted with one or more substituents selected from a fluorine atom, a $C_{1-3}$ alkyl group and a $C_{1-3}$ fluoroalkyl group (preferably, a $C_{1-3}$ perfluoroalkyl group).

In another embodiment, examples of X include, for example, the following groups:

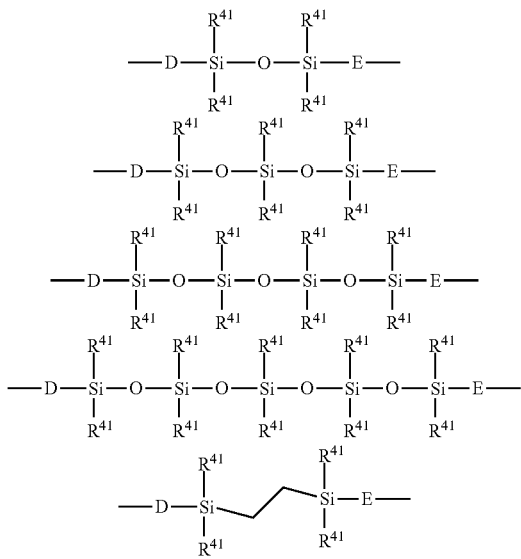

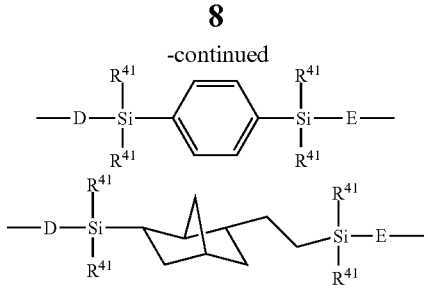

wherein $R^{41}$ is each independently a hydrogen atom, a phenyl group, an alkyl group having 1-6 carbon atoms, or a $C_{1-6}$ alkoxy group, preferably a methyl group;

D is a group selected from:
—CH$_2$O(CH$_2$)$_2$—,
—CH$_2$O(CH$_2$)$_3$—,
—CF$_2$O(CH$_2$)$_3$—,
—(CH$_2$)$_2$—,
—(CH$_2$)$_3$—,
—(CH$_2$)$_4$—,
—CONH—(CH$_2$)$_3$—,
—CON(CH$_3$)—(CH$_2$)$_3$—,
—CON(Ph)-(CH$_2$)$_3$— (wherein Ph is a phenyl group), and

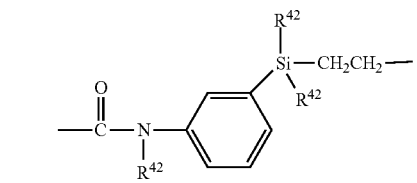

wherein $R^{42}$ is each independently a hydrogen atom, a $C_{1-6}$ alkyl group, or a $C_{1-6}$ alkoxy group, preferably a methyl group or a methoxy group, more preferably a methyl group, E is —(CH$_2$)$_n$— wherein n is an integer of 2-6, and
D binds to PFPE of the main backbone, and E binds to a group opposite to PFPE.

Specific examples of X include, for example:
—CH$_2$O(CH$_2$)$_2$—,
—CH$_2$O(CH$_2$)$_3$—,
—CH$_2$O(CH$_2$)$_6$—,
—CH$_2$O(CH$_2$)$_3$Si(CH$_3$)$_2$OSi(CH$_3$)$_2$(CH$_2$)$_2$—,
—CH$_2$O(CH$_2$)$_3$Si(CH$_3$)$_2$OSi(CH$_3$)$_2$OSi(CH$_3$)$_2$(CH$_2$)$_2$—,
—CH$_2$O(CH$_2$)$_3$Si(CH$_3$)$_2$O(Si(CH$_3$)$_2$O)$_2$Si(CH$_3$)$_2$(CH$_2$)$_2$—,
—CH$_2$O(CH$_2$)$_3$Si(CH$_3$)$_2$O(Si(CH$_3$)$_2$O)$_3$Si(CH$_3$)$_2$(CH$_2$)$_2$—,
—CH$_2$O(CH$_2$)$_3$Si(CH$_3$)$_2$O(Si(CH$_3$)$_2$O)$_{10}$Si(CH$_3$)$_2$(CH$_2$)$_2$—,
—CH$_2$O(CH$_2$)$_3$Si(CH$_3$)$_2$O(Si(CH$_3$)$_2$O)$_{20}$Si(CH$_3$)$_2$(CH$_2$)$_2$—,
—CH$_2$OCF$_2$CHFOCF$_2$—,
—CH$_2$OCF$_2$CHFOCF$_2$CF$_2$—,
—CH$_2$OCF$_2$CHFOCF$_2$CF$_2$CF$_2$—,
—CH$_2$OCH$_2$CF$_2$CF$_2$OCF$_2$—,
—CH$_2$OCH$_2$CF$_2$CF$_2$OCF$_2$CF$_2$—,
—CH$_2$OCH$_2$CF$_2$CF$_2$OCF$_2$CF$_2$CF$_2$—,
—CH$_2$OCH$_2$CF$_2$CF$_2$OCF(CF$_3$)CF$_2$OCF$_2$—,
—CH$_2$OCH$_2$CFCF$_2$OCF(CF$_3$)CF$_2$OCF$_2$CF$_2$—,
—CH$_2$OCH$_2$CF$_2$CF$_2$OCF(CF$_3$)CF$_2$OCF$_2$CF$_2$CF$_2$—,
—CH$_2$OCH$_2$CHFCF$_2$OCF$_2$—,
—CH$_2$OCH$_2$CHFCF$_2$OCF$_2$CF$_2$—,
—CH$_2$OCH$_2$CHFCF$_2$OCF$_2$CF$_2$CF$_2$—,
—CH$_2$OCH$_2$CHFCF$_2$OCF(CF$_3$)CF$_2$OCF$_2$—, —CH$_2$OCH$_2$CHFCF$_2$OCF(CF$_3$)CF$_2$OCF$_2$CF$_2$—,
—CH$_2$OCH$_2$CHFCF$_2$OCF(CF$_3$)CF$_2$OCF$_2$CF$_2$CF$_2$—
—CH$_2$OCH$_2$ (CH$_2$)$_7$CH$_2$Si(OCH$_3$)$_2$OSi(OCH$_3$)$_2$(CH$_2$)$_2$Si(OCH$_3$)$_2$OSi(OCH$_3$)$_2$ (CH$_2$)$_2$—,
—CH$_2$OCH$_2$CH$_2$CH$_2$Si(OCH$_3$)$_2$OSi(OCH$_3$)$_2$(CH$_2$)$_3$—,
—(CH$_2$)$_2$—,
—(CH$_2$)$_3$—,
—(CH$_2$)$_4$—,
—(CH$_2$)$_5$—,
—(CH$_2$)$_6$—,
—CONH—(CH$_2$)$_3$—,
—CON(CH$_3$)—(CH$_2$)$_3$—,
—CON(Ph)-(CH$_2$)$_3$— (wherein Ph is phenyl),
—CONH—(CH$_2$)$_6$—,
—CON(CH$_3$)—(CH$_2$)$_6$—,
—CON(Ph)-(CH$_2$)$_6$— (wherein Ph is phenyl),
—CONH—(CH$_2$)$_2$NH(CH$_2$)$_3$—,
—CONH—(CH$_2$)$_6$NH(CH$_2$)$_3$—,
—CH$_2$O—CONH—(CH$_2$)$_3$—,
—CH$_2$O—CONH—(CH$_2$)$_6$—,
—S—(CH$_2$)$_3$—,
—(CH$_2$)$_2$S(CH$_2$)$_3$—,
—CONH—(CH$_2$)$_3$Si(CH$_3$)$_2$OSi(CH$_3$)$_2$(CH$_2$)$_2$—,
—CONH—(CH$_2$)$_3$Si(CH$_3$)$_2$OSi(CH$_3$)$_2$OSi(CH$_3$)$_2$(CH$_2$)$_2$—,
—CONH—(CH$_2$)$_3$Si(CH$_3$)$_2$O(Si(CH$_3$)$_2$O)$_2$Si(CH$_3$)$_2$(CH$_2$)$_2$—,
—CONH—(CH$_2$)$_3$Si(CH$_3$)$_2$O(Si(CH$_3$)$_2$O)$_3$Si(CH$_3$)$_2$(CH$_2$)$_2$—,
—CONH—(CH$_2$)$_3$Si(CH$_3$)$_2$O(Si(CH$_3$)$_2$O)$_{10}$Si(CH$_3$)$_2$(CH$_2$)$_2$—,
—CONH—(CH$_2$)$_3$Si(CH$_3$)$_2$O(Si(CH$_3$)$_2$O)$_{20}$Si(CH$_3$)$_2$(CH$_2$)$_2$—
—C(O)O—(CH$_2$)$_3$—,
—C(O)O—(CH$_2$)$_6$—,
—CH$_2$—O—(CH$_2$)$_3$Si(CH$_3$)$_2$(CH$_2$)$_2$Si(CH$_3$)$_2$—(CH$_2$)$_3$—,
—CH$_2$—O—(CH$_2$)$_3$—Si(CH$_3$)$_2$—(CH$_2$)$_2$Si(CH$_3$)$_2$—H(CH$_3$)$_3$—,
—CH$_2$—O—(CH$_2$)$_3$—Si(CH$_3$)$_2$(CH$_2$)$_2$Si(CH$_3$)$_2$—CH(CH$_3$)—CH$_2$—,
—CH$_2$-O—(CH$_2$)$_3$—Si(CH$_3$)$_2$—(CH$_2$)$_2$—Si(CH$_3$)$_2$—CH(CH$_3$)—CH$_2$—,
—OCH$_2$H—,
—O(CH$_2$)$_3$—,
—OCFHCF$_2$—,

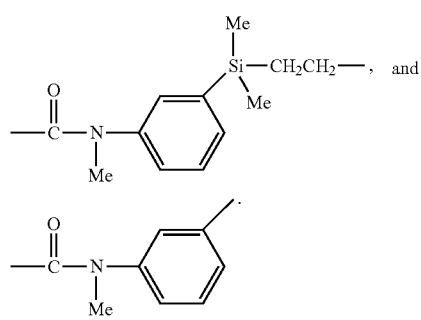

In another embodiment, X is each independently a 3-10 valent organic group.

In this embodiment, examples of X include the following groups:

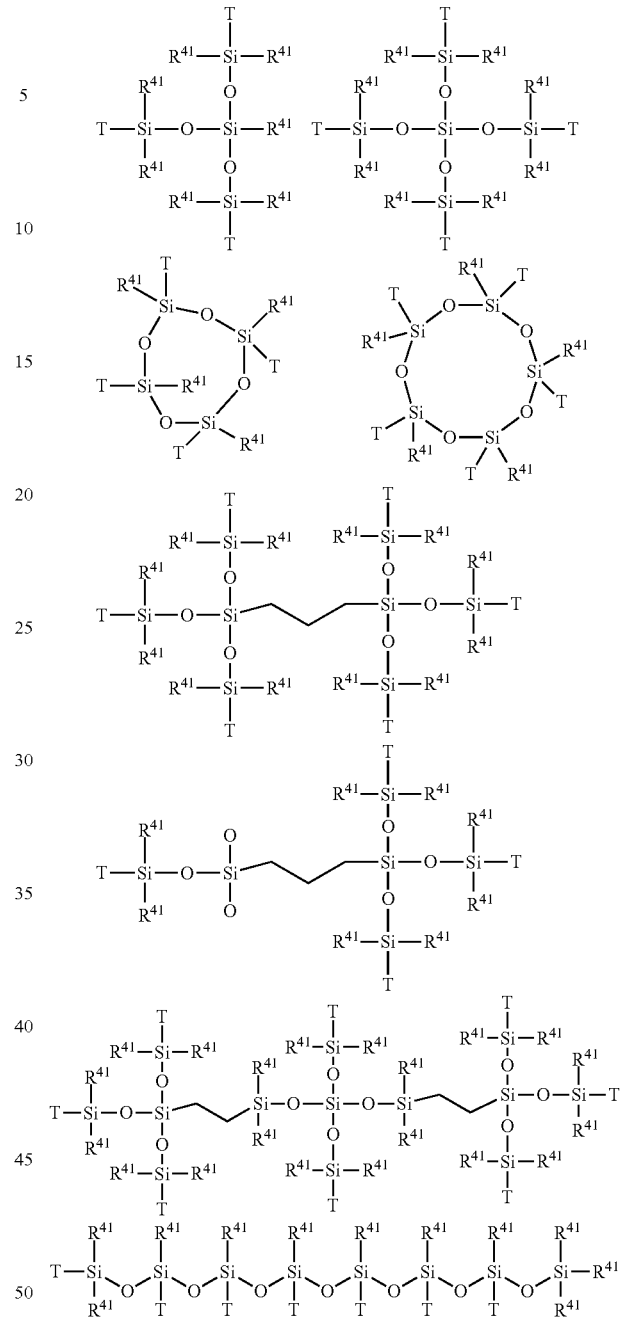

wherein R$^{41}$ is each independently a hydrogen atom, a phenyl group, an alkyl group having 1-6 carbon atoms, or a C$_{1-6}$ alkoxy group, preferably a methyl group;
in each X$^1$, some of T are a following group which binds to PFPE of the main backbone of the formula (1a) and (1b):
—CH$_2$O(CH$_2$)$_2$—,
—CH$_2$O(CH$_2$)$_3$—,
—CF$_2$O(CH$_2$)$_3$—,
—(CH$_2$)$_2$—,
—(CH$_2$)$_3$—,
—(CH$_2$)$_4$—,
—CONH—(CH$_2$)$_3$—,
—CON(CH$_3$)—(CH$_2$)$_3$—,
—CON(Ph)-(CH$_2$)$_3$— (wherein Ph is phenyl), or

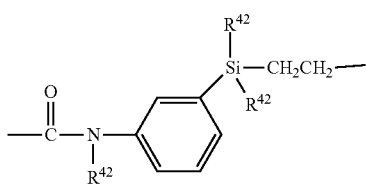

wherein $R^{42}$ is each independently a hydrogen atom, a $C_{1-6}$ alkyl group, or a $C_{1-6}$ alkoxy group, preferably a methyl group or a methoxy group, more preferably a methyl group, some of the other T are —$(CH_2)_{n''}$— (wherein n" is an integer of 2-6) attached to the group opposite to PFPE which is a molecular backbone (i.e., —$CR^a_k R^b_l R^c_m$ in the formula (1a) and (1b)), and the others T are each independently a methyl group, a phenyl group, or a $C_{1-6}$ alkoxy, if present.

In the formula, $R^a$ is each independently at each occurrence —Z—$CR^1_p R^2_q R^3_r$.

In the formula, Z is each independently at each occurrence, an oxygen atom or a divalent organic group.

Z is preferably a $C_{1-6}$ alkylene group, —$(CH_2)_g$—O—$(CH_2)_h$— (wherein g is an integer of 0-6, for example, an integer of 1-6, h is an integer of 0-6, for example, an integer of 1-6) or -phenylene-$(CH_2)_i$— (wherein i is an integer of 0-6), more preferably a $C_{1-3}$ alkylene group. These groups may be substituted with, for example, one or more substituents selected form a fluorine atom, a $C_{1-6}$ alkyl group, a $C_{2-6}$ alkenyl group, and a $C_{2-6}$ alkynyl group.

In the formula, $R^1$ is each independently at each occurrence $R^{a\prime}$. $R^{a\prime}$ is as defined for $R^a$.

In $R^a$, the number of C atoms which are linearly connected via Z is up to five. That is, in $R^a$, when there is at least one $R^1$, there are two or more C atoms which are linearly connected via Z in $R^a$. The number of such C atoms which are linearly connected via Z is five at most. It is noted that "the number of such C atoms which are linearly connected via Z in $R^a$ is equal to the repeating number of —Z—C— which are linearly connected in $R^a$.

For example, one example in which C atoms are connected via Z in $R^a$ is shown below.

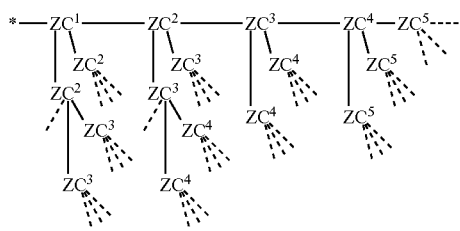

In the above formula, * represents a position binding to C of the main backbone, and . . . represents that a predetermined group other than ZC binds thereto, that is, when all three bonds of a C atom are . . . , it means an end point of the repeat of ZC. The number on the right shoulder of C means the number of occurrences of C which is linearly connected via the Z group from *. In other words, in the chain in which the repeat of ZC is completed at $C^2$, "the number of such C atoms which are linearly connected via the Z group in $R^{a\prime\prime\prime}$" is 2. Similarly, in the chain in which the repeat of ZC is completed at $C^3$, $C^4$ and $C^5$, respectively, "the number of such C atoms which are linearly connected via the Z group in $R^{a\prime\prime\prime}$" is 3, 4 and 5. It is noted that as seen from the above formula, there are some ZC chains, but they need not have the same length and may be have arbitrary length.

In a preferred embodiment, as shown below, "the number of such C atoms which are linearly connected via the Z group in $R^{a\prime\prime\prime}$" is 1 (left formula) or 2 (right formula) in all chains.

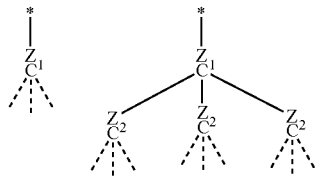

In one embodiment, the number of such C atoms which are linearly connected via the Z group in $R^a$ is 1 or 2, preferably 1.

In the formula, $R^2$ is —Y—$SiR^5_n R^6_{3-n}$.

Y is each independently at each occurrence a divalent organic group.

In a preferable embodiment, Y is a $C_{1-6}$ alkylene group, —$(CH_2)_{g'}$—O—$(CH_2)_{h'}$— (wherein g' is an integer of 0-6, for example, an integer of 1-6, and h' is an integer of 0-6, for example, an integer of 1-6), or -phenylene-$(CH_2)_{i'}$— (wherein i' is an integer of 0-6). These groups may be substituted with, for example, one or more substituents selected form a fluorine atom, a $C_{1-6}$ alkyl group, a $C_{2-6}$ alkenyl group, and a $C_{2-6}$ alkynyl group.

In one embodiment, Y may be a $C_{1-6}$ alkylene group, —O—$(CH_2)_{h'}$— or -phenylene-$(CH_2)_{i'}$—. When Y is the above group, a light resistance, in particular an ultraviolet resistance, may be increased.

$R^5$ is each independently at each occurrence a hydroxyl group or a hydrolyzable group.

The "hydrolyzable group" as used herein represents a group which is able to undergo a hydrolysis reaction.

Examples of the hydrolyzable group include —OR, —OCOR, —O—N=$C(R)_2$, —$N(R)_2$, —NHR, halogen (wherein R is a substituted or non-substituted alkyl group having 1-4 carbon atoms), preferably —OR (an alkoxy group). Examples of R include a non-substituted alkyl group such as a methyl group, an ethyl group, a propyl group, an isopropyl group, a n-butyl group, an isobutyl group; a substituted alkyl group such as a chloromethyl group. Among them, an alkyl group, in particular a non-substituted alkyl group is preferable, a methyl group or an ethyl group is more preferable. The hydroxyl group may be, but is not particularly limited to, a group generated by hydrolysis of a hydrolyzable group.

Preferably, $R^5$ is —OR wherein R is a substituted or unsubstituted $C_{1-3}$ alkyl group, more preferably an ethyl group or a methyl group, in particular a methyl group.

In the formula, $R^6$ is each independently at each occurrence a hydrogen atom or a lower alkyl group. The lower alkyl group is preferably an alkyl group having 1-20 carbon atoms, more preferably an alkyl group having 1-6 carbon atoms, further preferably a methyl group.

n is an integer of 1-3, preferably 2 or 3, more preferably 3, independently per unit —Y—$SiR^5_n R^6_{3-n}$.

In the formula, $R^3$ is each independently at each occurrence a hydrogen atom or a lower alkyl group. The lower alkyl group is preferably an alkyl group having 1-20 carbon atoms, more preferably an alkyl group having 1-6 carbon atoms, further preferably a methyl group.

In the formula, p is each independently at each occurrence an integer of 0-3; q is each independently at each occurrence an integer of 0-3; r is each independently at each occurrence an integer of 0-3. The sum of p, q and r is 3.

In a preferable embodiment, in $R^{a'}$ (when $R^{a'}$ is absent, $R^a$) at the terminal of $R^a$, q is preferably 2 or more, for example 2 or 3, more preferably 3.

In the formula, $R^b$ is each independently at each occurrence —Y—SiR$^5_n$R$^6_{3-n}$. Y, R$^5$, R$^6$ and n are as defined for $R^2$.

In the formula, $R^c$ is each independently at each occurrence a hydrogen atom or a lower alkyl group. The lower alkyl group is preferably an alkyl group having 1-20 carbon atoms, more preferably an alkyl group having 1-6 carbon atoms, further preferably a methyl group.

In the formula, k is each independently at each occurrence an integer of 0-3; l is each independently at each occurrence an integer of 0-3; and m is each independently at each occurrence an integer of 0-3. The sum of k, l and m is 3.

In one embodiment, at least one k is 2 or 3, preferably 3.

In one embodiment, k is 2 or 3, preferably 3.

In one embodiment, l is 2 or 3, preferably 3.

In the formula (1a) and (1b), at least one q is 2 or 3, or at least one l is 2 or 3. That is, there are at least two —Y—SiR$^5_n$R$^6_{3-n}$ groups in the formula.

In the perfluoro(poly)ether group containing silane compound of the formula (1a) or the formula (1b), an average molecular weight of the Rf-PFPE moiety is not particularly limited to, and is 500-30,000, preferably 1,500-30,000, more preferably 2,000-10,000.

The perfluoro(poly)ether group containing silane compound of the formula (1a) or the formula (1b) may have, but are not limited to, an average molecular weight of 5×10$^2$- 1×10$^5$. Among such range, in view of friction durability, the compound has preferably 2,000-32,000, more preferably 2,500-12,000. It is noted that the "average molecular weight" in the present invention means a number average molecular weight, and the "average molecular weight" is defined as a value measured by using $^{19}$F-NMR.

The perfluoro(poly)ether group containing silane compound of the formula (1a) or the formula (1b) can be prepared by a combination of known methods. For example, a compound of the formula (1a') wherein X is a divalent group can be prepared below, although the present invention is not limited thereto.

A group containing a double bond (preferably allyl), and a halogen (preferably bromo) are introduced into polyol of HO—X—C(YOH)$_3$ (wherein X and Y are each independently a divalent organic group) to obtain a halide having a double bond of Hal-X—C(Y—O—R—CH=CH$_2$)$_3$ (wherein Hal is halogen, for example Br, and R is a divalent organic group, for example an alkylene group). Then, halogen at the terminal is reacted with a perfluoropolyether group containing alcohol of R$^{PFPE}$—OH (wherein R$^{PFPE}$ is a perfluoropolyether group containing group.) to obtain R$^{PFPE}$—O—X—C(Y—O—R—CH=CH$_2$)$_3$. Then, —CH=CH$_2$ at the terminal is reacted with HSiCl$_3$ and an alcohol or HSiR$^5_3$ to obtain R$^{PFPE}$—O—X—C(Y—O—R—CH$_2$—CH$_2$—SiR$^5_3$)$_3$.

Those skilled in the art can appropriately select a preferable range of a reaction condition for preparing the perfluoro(poly)ether group containing silane compound of the present invention can be selected by those skilled in the art.

Next, the surface-treating agent of the present invention will be described.

The surface-treating agent of the present invention comprises at least one the perfluoro(poly)ether group containing silane compound of the formula (1a) or the formula (1b).

The surface-treating agent of the present invention can provide a base material with water-repellency, oil-repellency, antifouling property, surface slip property and friction durability, and can be suitably used as an antifouling-coating agent or a water-proof coating agent, although the present invention is not particularly limited thereto.

In one embodiment, the surface-treating agent of the present invention comprises at least one compound of the formula (1a) or the formula (1b) wherein x is a divalent organic group, α and β are 1.

In one embodiment, the surface-treating agent of the present invention comprises at least one compound of the formula (1a) or the formula (1b) wherein l is 3 and n is 3.

In one embodiment, the surface-treating agent of the present invention comprises the compound of the formula (1a).

The above-mentioned surface-treating agent may comprise other components in addition to the compound of the formula (1a) or the formula (1b). Examples of the other components include, but are not particularly limited to, for example, a (non-reactive) fluoropolyether compound which may be also understood as a fluorine-containing oil, preferably a perfluoro(poly)ether compound (hereinafter, referred to as "the fluorine-containing oil"), a (non-reactive) silicone compound which may be also understood as a silicone oil (hereinafter referred to as "a silicone oil"), a catalyst, and the like.

Examples of the above-mentioned fluorine-containing oil include, but are not particularly limited to, for example, a compound of the following general formula (3) (a perfluoro(poly)ether compound).

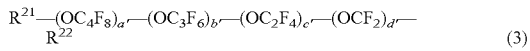

(3)

In the formula, $R^{21}$ represents a $C_{1-16}$ alkyl group which may be substituted by one or more fluorine atoms (preferably, a $C_{1-16}$ perfluoroalkyl group), $R^{22}$ represents a $C_{1-16}$ alkyl group which may be substituted by one or more fluorine atoms (preferably, a $C_{1-16}$ perfluoroalkyl group), a fluorine atom or a hydrogen atom, and more preferably, $R^{21}$ and $R^{22}$ is each independently a $C_{1-3}$ perfluoroalkyl group.

Subscripts a', b', c' and d' represent the repeating number of each of four repeating units of perfluoropolyether which constitute a main backbone of the polymer, and are each independently an integer of 0 or more and 300 or less, and the sum of a', b', c' and d' is at least 1, preferably 1-300, more preferably 20-300. The occurrence order of the respective repeating units in parentheses with the subscript a', b', c' or d' is not limited in the formulae. Among these repeating units, the —(OC$_4$F$_8$)— group may be any of —(OCF$_2$CF$_2$CF$_2$CF$_2$)—, —(OCF(CF$_3$)CF$_2$CF$_2$)—, —(OCF$_2$CF(CF$_3$)CF$_2$)—, —(OCF$_2$CF$_2$CF(CF$_3$))—, —(OC(CF$_3$)$_2$CF$_2$)—, —(OCF$_2$C(CF$_3$)$_2$)—, —(OCF(CF$_3$)CF(CF$_3$))—, —(OCF(C$_2$F$_5$)CF$_2$)— and —(OCF$_2$CF(C$_2$F$_5$))—, preferably —(OCF$_2$CF$_2$CF$_2$CF$_2$)—. The —(OC$_3$F$_6$)— group may be any of —(OCF$_2$CF$_2$CF$_2$)—, —(OCF(CF$_3$)CF$_2$)— and —(OCF$_2$CF(CF$_3$))—, preferably —(OCF$_2$CF$_2$CF$_2$)—. The —(OC$_2$F$_4$)— group may be any of —(OCF$_2$CF$_2$)— and —(OCF(CF$_3$))—, preferably —(OCF$_2$CF$_2$)—.

Examples of the perfluoropolyether compound of the above general formula (3) include a compound of any of the following general formulae (3a) and (3b) (may be one compound or a mixture of two or more compounds).

(3a)

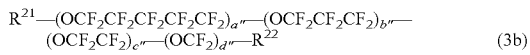

(3b)

In these formulae:

$R^{21}$ and $R^{22}$ are as defined above; in the formula (3a), b" is an integer of 1 or more and 100 or less; and in the formula (3b), a" and b" are each independently an integer of 0 or more and 30 or less, and c" and d" are each independently an integer of 1 or more and 300 or less. The occurrence order of the respective repeating units in parentheses with the subscript a", b", c" or d" is not limited in the formulae.

The above-mentioned fluorine-containing oil may have an average molecular weight of 1,000-30,000. By having such average molecular weight, high surface slip property can be obtained.

The fluorine-containing oil may be contained in the surface-treating agent of the present invention, for example, at 0-500 parts by mass, preferably 0-400 parts by mass, more preferably 25-400 parts by mass with respect to 100 parts by mass of the PFPE containing silane compound of the present invention (as the total mass when two or more compounds are used; hereinafter the same shall apply).

The compound of the general formula (3a) and the compound of the general formula (3b) may be used alone or in combination. The compound of the general formula (3b) is preferable than the compound of the general formula (3a) since the compound of the general formula (3b) provides higher surface slip property than the compound of the general formula (3a). When they are used in combination, the ratio by mass of the compound of the general formula (3a) to the compound of the general formula (3b) is preferably 1:1 to 1:30, more preferably 1:1 to 1:10. By applying such ratio by mass, a perfluoropolyether group-containing silane-based coating which provides a good balance of surface slip property and friction durability can be obtained.

In one embodiment, the fluorine-containing oil comprises one or more compounds of the general formula (3b). In such embodiment, the mass ratio of the compound of the formula (1a) or the formula (1b) to the compound of the formula (3b) in the surface-treating agent is preferably 4:1 to 1:4.

In one preferable embodiment, the surface-treating agent of the present invention comprises the compound of the formula (1a) or the formula (1b) wherein PFPE is $-(OCF_2CF_2CF_2)_b-$ (b is an integer of 1-200) and the compound of the formula (3b). By forming a surface-treating layer by using such surface-treating agent with a wet coating method or a vacuum deposition method, preferably vacuum deposition, excellent surface slip property and friction durability can be obtained.

In one preferable embodiment, the surface-treating agent of the present invention comprises the compound wherein PFPE represents $-(OC_4F_8)_a-(OC_3F_6)_b-(OC_2F_4)_c-(OCF_2)_d-$ wherein a and b are each independently an integer of 0 or more and 30 or less, preferably 0 or more and 10 or less, and c and d are each independently an integer of 1 or more and 200 or less, and the sum of a, b, c and d is an integer of 10 or more and 200 or less. The occurrence order of the respective repeating units in parentheses with the subscript a, b, c or d is not limited in the formula and the compound of the formula (3b). By forming a surface-treating layer by using such surface-treating agent with a wet coating method or a vacuum deposition method, preferably vacuum deposition, more excellent surface slip property and friction durability can be obtained.

In these embodiments, an average molecular weight of the compound of the formula (3a) is preferably 2,000-8,000.

In these embodiments, an average molecular weight of the compound of the formula (3b) is preferably 2,000-30,000. An average molecular weight of the compound of the formula (3b) is preferably 8,000-30,000 when a surface-treating layer is formed by a dry coating method, for example, vacuum deposition, and is preferably 2,000-10,000, in particular 3,000-5,000 when a surface-treating layer is formed by using a wet coating method, for example, spray coating.

In a preferable embodiment, when a surface-treating layer is formed by using vacuum deposition, an average molecular weight of the fluorine-containing oil may be higher than an average molecular weight of the compound of the formula (1a) and the formula (1b). By selecting such average molecular weights of the compound of the formula (1a) and the formula (1b) and the fluorine-containing oil, more excellent surface slip property and friction durability can be obtained.

From the other point of view, the fluorine-containing oil may be a compound of the general formula Rf'-F wherein Rf' is a $C_{5-16}$ perfluoroalkyl group. The compound of Rf'-F is preferable because the compound has high affinity for the compound of the formula (1a) and the formula (1b) wherein Rf is a $C_{1-16}$ perfluoroalkyl group.

The fluorine-containing oil contributes to increasing of surface slip property of the surface-treating layer.

Examples of the above-mentioned silicone oil include, for example, a liner or cyclic silicone oil having 2,000 or less siloxane bonds. The liner silicone oil may be so-called a straight silicone oil and a modified silicon oil. Examples of the straight silicone oil include dimethylsilicone oil, methylphenylsilicone oil, and methylhydrogensilicone oil. Examples of the modified silicone oil include that which is obtained by modifying a straight silicone oil with alkyl, aralkyl, polyether, higher fatty acid ester, fluoroalkyl, amino, epoxy, carboxyl, alcohol, or the like. Examples of the cyclic silicone oil include, for example, cyclic dimethylsiloxane oil.

The silicone oil may be contained in the surface-treating agent of the present invention, for example, at 0-300 parts by mass, preferably 50-200 parts by mass with respect to 100 parts by mass of the PFPE containing silane compound of the present invention (as the total mass when two or more compounds are used; hereinafter the same shall apply).

The silicone oil contributes to increasing of surface slip property of the surface-treating layer.

Examples of the above-mentioned catalyst include an acid (for example, acetic acid, trifluoroacetic acid, etc.), a base (for example, ammonia, triethylamine, diethylamine, etc.), a transition metal (for example, Ti, Ni, Sn, etc.), and the like.

The catalyst facilitates hydrolysis and dehydration-condensation of the PFPE containing silane compound of the present invention to facilitate a formation of the surface-treating layer.

Examples of the other components other than the above-mentioned components include, for example, tetraethoxysilane, methyltrimethoxysilane, 3-aminopropyltrimethoxysilane, 3-glycidoxypropyltrimethoxysilane, methyltriacetoxysilane, and the like.

The surface-treating agent of the present invention is impregnated into a porous material, for example, a porous ceramic material, a metal fiber for example that obtained by solidifying a steel wool to obtain a pellet. The pellet can be used, for example, in vacuum deposition.

Next, the article of the present invention will be described.

The article of the present invention comprises a base material and a layer (surface-treating layer) which is formed from the PFPE containing silane compound or the surface-treating agent of the present invention (hereinafter, referred to simply as "surface-treating agent" as a representative thereof) on the surface of the base material. This article can be produced, for example, as follows.

Firstly, the base material is provided. The base material usable in the present invention may be composed of any suitable material such as a glass, a resin (may be a natural or synthetic resin such as a common plastic material, and may be in form of a plate, a film, or others), a metal (may be a simple substance of a metal such as aluminum, copper, or iron, or a complex such as alloy or the like), a ceramic, a semiconductor (silicon, germanium, or the like), a fiber (a fabric, a non-woven fabric, or the like), a fur, a leather, a wood, a pottery, a stone, an architectural member or the like.

For example, when an article to be produced is an optical member, a material constituting the surface of the base material may be a material for an optical member, for example, a glass or a transparent plastic. For example, when an article to be produced is an optical member, any layer (or film) such as a hard coating layer or an antireflection layer may be formed on the surface (outermost layer) of the base material. As the antireflection layer, either a single antireflection layer or a multi antireflection layer may be used. Examples of an inorganic material usable in the antireflection layer include $SiO_2$, SiO, $ZrO_2$, $TiO_2$, TiO, $Ti_2O_3$, $Ti_2O_5$, $Al_2O_3$, $Ta_2O_5$, $CeO_2$, MgO, $Y_2O_3$, $SnO_2$, $MgF_2$, $WO_3$, and the like. These inorganic materials may be used alone or in combination with two or more (for example, as a mixture). When multi antireflection layer is formed, preferably, $SiO_2$ and/or SiO are used in the outermost layer. When an article to be produced is an optical glass part for a touch panel, it may have a transparent electrode, for example, a thin layer comprising indium tin oxide (ITO), indium zinc oxide, or the like on a part of the surface of the base material (glass). Furthermore, the base material may have an insulating layer, an adhesive layer, a protecting layer, a decorated frame layer (I-CON), an atomizing layer, a hard coating layer, a polarizing film, a phase difference film, a liquid crystal display module, and the like, depending on its specific specification.

The shape of the base material is not specifically limited. The region of the surface of the base material on which the surface-treating layer should be formed may be at least a part of the surface of the base material, and may be appropriately determined depending on use, the specific specification, and the like of the article to be produced.

The base material may be that of which at least the surface consists of a material originally having a hydroxyl group. Examples of such material include a glass, in addition, a metal on which a natural oxidized film or a thermal oxidized film is formed (in particular, a base metal), a ceramic, a semiconductor, and the like. Alternatively, as in a resin, when the hydroxyl groups are present but not sufficient, or when the hydroxyl group is originally absent, the hydroxyl group can be introduced on the surface of the base material, or the number of the hydroxyl group can be increased by subjecting the base material to any pretreatment. Examples of the pretreatment include a plasma treatment (for example, corona discharge) or an ion beam irradiation. The plasma treatment may be suitably used to introduce the hydroxyl group into or increase it on the surface of the base material, further, to clarify the surface of the base material (remove foreign materials, and the like). Alternatively, other examples of the pretreatment include a method wherein a monolayer of a surface adsorbent having a carbon-carbon unsaturated bond group is formed on the surface of the base material by using a LB method (Langmuir-Blodgett method) or a chemical adsorption method beforehand, and then, cleaving the unsaturated bond under an atmosphere of oxygen and nitrogen.

Alternatively, the base material may be that of which at least the surface consists of a material comprising other reactive group such as a silicon compound having one or more Si—H groups or alkoxysilane.

Next, the film of the above surface-treating agent of the present invention is formed on the surface of the base material, and the film is post-treated, as necessary, and thereby the surface-treating layer is formed from the surface-treating agent.

The formation of the film of the surface-treating agent of the present invention can be performed by applying the above surface-treating agent on the surface of the base material such that the surface-treating agent coats the surface. The method of coating is not specifically limited. For example, a wet coating method or a dry coating method can be used.

Examples of the wet coating method include dip coating, spin coating, flow coating, spray coating, roll coating, gravure coating, and a similar method.

Examples of the dry coating method include deposition (usually, vacuum deposition), sputtering, CVD and a similar method. The specific examples of the deposition method (usually, vacuum deposition) include resistance heating, electron beam, high-frequency heating using microwave, etc., ion beam, and a similar method. The specific examples of the CVD method include plasma-CVD, optical CVD, thermal CVD and a similar method. The deposition method is will be described below in more detail.

Additionally, coating can be performed by an atmospheric pressure plasma method.

When the wet coating method is used, the surface-treating agent of the present invention is diluted with a solvent, and then it is applied to the surface of the base material. In view of stability of the surface-treating agent of the present invention and volatile property of the solvent, the following solvents are preferably used: an aliphatic perfluorohydrocarbon having 5-12 carbon atoms (for example, perfluorohexane, perfluoromethylcyclohexane and perfluoro-1,3-dimethylcyclohexane); an aromatic polyfluorohydrocarbon (for example, bis(trifluoromethyl)benzene); an aliphatic polyfluorohydrocarbon (for example, $C_6F_{13}CH_2CH_3$ (for example, ASAHIKLIN (registered trademark) AC-6000 manufactured by Asahi Glass Co., Ltd.), 1,1,2,2,3,3,4-heptafluorocyclopentane (for example, ZEORORA (registered trademark) H manufactured by Nippon Zeon Co., Ltd.); a hydrofluoroether (HFE) (for example, an alkyl perfluoroalkyl ether such as perfluoropropyl methyl ether ($C_3F_7OCH_3$) (for example, Novec (trademark) 7000 manufactured by Sumitomo 3M Ltd.), perfluorobutyl methyl ether ($C_4F_9OCH_3$) (for example, Novec (trademark) 7100 manufactured by Sumitomo 3M Ltd.), perfluorobutyl ethyl ether ($C_4F_9OC_2H_5$) (for example, Novec (trademark) 7200 manufactured by Sumitomo 3M Ltd.), and perfluorohexyl methyl ether ($C_2F_5CF(OCH_3)C_3F_7$) (for example, Novec (trademark) 7300 manufactured by Sumitomo 3M Ltd.) (the perfluoroalkyl group and the alkyl group may be liner or branched)), or $CF_3CH_2OCF_2CHF_2$ (for example, ASAHIKLIN (registered trademark) AE-3000 manufactured by Asahi Glass Co., Ltd.) and the like. These solvents may be used alone or as a mixture of 2 or more compound. Among them, the hydrofluoroether is preferable, perfluorobutyl methyl ether ($C_4F_9OCH_3$) and/or perfluorobutyl ethyl ether ($C_4F_9OC_2H_5$) are particularly preferable.

When the dry coating method is used, the surface-treating agent of the present invention may be directly subjected to the dry coating method, or may be diluted with a solvent, and then subjected to the dry coating method.

The formation of the film is preferably performed so that the surface-treating agent of the present invention is present together with a catalyst for hydrolysis and dehydration-condensation in the coating. Simply, when the wet coating method is used, after the surface-treating agent of the present invention is diluted with a solvent, and just prior to applying it to the surface of the base material, the catalyst may be added to the diluted solution of the surface-treating agent of the present invention. When the dry coating method is used, the surface-treating agent of the present invention to which a catalyst has been added is used itself in deposition (usually, vacuum deposition), or pellets may be used in the deposition (usually, the vacuum deposition), wherein the pellets is obtained by impregnating a porous metal such as iron or copper with the surface-treating agent of the present invention to which the catalyst has been added.

As the catalyst, any suitable acid or base can be used. As the acid catalyst, for example, acetic acid, formic acid, trifluoroacetic acid, or the like can be used. As the base catalyst, for example, ammonia, an organic amine, or the like can be used.

Next, the film is post-treated as necessary. This post-treatment is, but not limited to, a treatment in which water supplying and dry heating are sequentially performed, in more particular, may be performed as follows.

After the film of the surface-treating agent of the present invention is formed on the surface of the base material as mentioned above, water is supplied to this film (hereinafter, referred to as precursor coating). The method of supplying water may be, for example, a method using dew condensation due to the temperature difference between the precursor coating (and the base material) and ambient atmosphere or spraying of water vapor (steam), but not specifically limited thereto.

It is considered that, when water is supplied to the precursor coating, water acts on a hydrolyzable group bonding to Si present in the perfluoro(poly)ether group containing silane compound in the surface-treating agent of the present invention, thereby enabling rapid hydrolysis of the compound.

The supplying of water may be performed under an atmosphere, for example, at a temperature of 0-250° C., preferably 60° C. or more, more preferably 100° C. or more and preferably 180° C. or less, more preferably 150° C. By supplying water at such temperature range, hydrolysis can proceed. The pressure at this time is not specifically limited but simply may be ambient pressure.

Then, the precursor coating is heated on the surface of the base material under a dry atmosphere over 60° C. The method of dry heating may be to place the precursor coating together with the base material in an atmosphere at a temperature over 60° C., preferably over 100° C., and for example, of 250° C. or less, preferably of 180° C. or less, and at unsaturated water vapor pressure, but not specifically limited thereto. The pressure at this time is not specifically limited but simply may be ambient pressure.

Under such atmosphere, between the PFPE containing silane compound of the present inventions, the groups (being hydroxyl groups when all $R^1$ are hydroxyl groups in the above mentioned compound of any of the formula (1a) or the formula (1b); hereinafter the same shall apply) bonding to Si after hydrolysis are rapidly dehydration-condensed with each other. Furthermore, between the compound and the base material, the group bonding to Si in the compound after hydrolysis and a reactive group present on the surface of the base material are rapidly reacted, and when the reactive group present on the surface of the base material is a hydroxyl group, dehydration-condensation is caused. As the result, the bond between the PFPE containing silane compounds of the present invention is formed, and the bond between the compound and the base material is formed. It is noted that if present, the fluorine-containing oil and/or the silicone oil is held or acquired by an affinity to the perfluoropolyether group containing silane compound.

The above supplying of water and dry heating may be sequentially performed by using a superheated water vapor.

The superheated water vapor is a gas which is obtained by heating a saturated water vapor to a temperature over the boiling point, wherein the gas, under an ambient pressure, has become to have a unsaturated water vapor pressure by heating to a temperature over 100° C., generally of 250° C. or less, for example, of 180° C. or less, and over the boiling point. When the base material on which the precursor coating is formed is exposed to a superheated water vapor, firstly, due to the temperature difference between the superheated water vapor and the precursor coating of a relatively low temperature, dew condensation is generated on the surface of the precursor coating, thereby supplying water to the precursor coating. Presently, as the temperature difference between the superheated water vapor and the precursor coating decreases, water on the surface of the precursor coating is evaporated under the dry atmosphere of the superheated water vapor, and an amount of water on the surface of the precursor coating gradually decreases. During the amount of water on the surface of the precursor coating is decreasing, that is, during the precursor coating is under the dry atmosphere, the precursor coating on the surface of the base material contacts with the superheated water vapor, as a result, the precursor coating is heated to the temperature of the superheated water vapor (temperature over 100° C. under ambient pressure). Therefore, by using a superheated water vapor, supplying of water and dry heating are enabled to be sequentially carried out simply by exposing the base material on which the precursor coating is formed to a superheated water vapor.

As mentioned above, the post-treatment can be performed. It is noted that though the post-treatment may be performed in order to further increase friction durability, it is not essential in the producing of the article of the present invention. For example, after applying the surface-treating agent to the surface of the base material, it may be enough to only stand the base material.

As described above, the surface-treating layer derived from the film of the surface-treating agent of the present invention is formed on the surface of the base material to produce the article of the present invention. The surface-treating layer thus formed has high surface slip property and high friction durability. Furthermore, this surface-treating layer may have water-repellency, oil-repellency, antifouling property (for example, preventing from adhering a fouling such as fingerprints), waterproof property (preventing the ingress of water into an electrical member, and the like), surface slip property (or lubricity, for example, wiping property of a fouling such as fingerprints and excellent tactile feeling in a finger) depending on a composition of the surface-treating agent used, in addition to high friction durability, thus may be suitably used as a functional thin film.

Therefore, the present invention further provides an optical material having the hardened material on the outermost layer.

Examples of the optical material include preferably a variety of optical materials in addition to the optical material for displays, or the like exemplified in below: for example, displays such as a cathode ray tube (CRT; for example, TV, personal computer monitor), a liquid crystal display, a plasma display, an organic EL display, an inorganic thin-film EL dot matrix display, a rear projection display, a vacuum fluorescent display (VFD), a field emission display (FED; Field Emission Display), or a protective plate of such displays, or that in which these displays and protective plates have been subjected to antireflection treatment on their surface.

The article having the surface-treating layer obtained according to the present invention is not specifically limited to, but may be an optical member. Examples of the optical member include the followings: lens of glasses, or the like; a front surface protective plate, an antireflection plate, a polarizing plate, or an anti-glare plate on a display such as PDP and LCD; a touch panel sheet of an instrument such as a mobile phone or a personal digital assistance; a disk surface of an optical disk such as a Blu-ray disk, a DVD disk, a CD-R or MO; an optical fiber, and the like.

The article having the surface-treating layer obtained according to the present invention may be also a medical equipment or a medical material.

The thickness of the surface-treating layer is not specifically limited. For the optical member, the thickness of the surface-treating layer is within the range of 1-50 nm, 1-30 nm, preferably 1-15 nm, in view of optical performance, surface slip property, friction durability and antifouling property.

Hereinbefore, the article produced by using the surface-treating agent of the present invention is described in detail. It is noted that an application, a method for using or a method for producing the article are not limited to the above exemplification.

EXAMPLES

The surface-treating agent of the present invention will be described in detail through Examples, although the present invention is not limited to Examples. It is noted that the occurrence order of the four repeating units ($CF_2O$), ($CF_2CF_2O$), ($CF(CF_3)CF_2O$), ($CF_2CF_2CF_2O$) and ($CF_2CF_2CF_2CF_2O$) constituting the perfluoropolyether of is not limited in Examples.

Synthesizing Example 1

To a four necked flask of 100 mL provided with a reflux condenser, a thermometer and a stirrer, NaH (4.62 g), and tetrabutylammonium bromide (0.41 g) were added. Then, 1,3-bis(trifluoromethyl)benzene (23 g), 1,4-dibromobutane (42 g), and pentaerythritol triallyl ether (10 g) were added and stirred at 65° C., and then separated and purified to obtain pentaerythritol triallyl ether bromo adduct (A) (5.23 g).

Pentaerythritol triallyl ether bromo adduct (A):
$BrCH_2CH_2CH_2CH_2CH_2OCH_2C(CH_2CH_2CH=CH_2)_3$ Synthesizing Example 2

To a four necked flask of 100 mL provided with a reflux condenser, a thermometer and a stirrer, a perfluoropolyether modified alcohol compound of the average composition: $CF_3O(CF_2CF_2O)_{20}(CF_2O)_{16}CF_2CH_2OH$ (with proviso that although the compound comprising a small amount of the repeating units ($CF_2CF_2CF_2O$) and/or ($CF_2CF_2CF_2O$) in the mixture, it was not taken into consideration since it was a very small amount) (8.96 g), 1,3-bis(trifluoromethyl)benzene (51 g), and KOH (0.39 g) were added and stirred at 70° C. Then, pentaerythritol triallyl ether bromo adduct (A) (3.60 g) obtained in Synthesizing Example 1, and tetrabutylammonium bromide (0.14 g) were added and stirred at 70° C., and then separated and purified to obtain perfluoropolyether group containing allyloxy compound (B) having an allyl group at the terminal (4.86 g).

Perfluoropolyether group containing allyloxy compound (B):

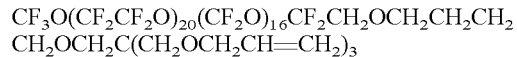

Synthesizing Example 3

To a four necked flask of 50 mL provided with a reflux condenser, a thermometer and a stirrer, perfluoropolyether group containing allyloxy compound (B) (3.33 g) obtained in Synthesizing Example 2, 1,3-bis(trifluoromethyl)benzene (7.24 g), and triacetoxysilane (0.01 g) were added and stirred for 30 minutes. Then, trichlorosilane (1.16 g) and a xylene solution (0.03 ml) containing Pt complex of 1,3-divinyl-1,1,3,3-tetramethyldisiloxane at 2% were added and stirred at 60° C. for 3 hours. Then, volatile content was distilled off under a reduced pressure to obtain, and a mixture of methanol (0.13 g) and trimethyl orthoformate (5.25 g) was added, and then, stirred at 50° C. and separate and purified to obtain perfluoropolyether group containing silane compound (C) having trimethoxysilyl group at the terminal (3.12 g).

Perfluoropolyether group containing silane compound (C):

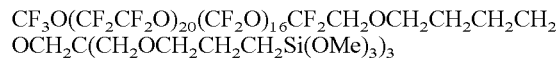

Synthesizing Example 4

To a four necked flask of 100 mL provided with a reflux condenser, a thermometer and a stirrer, perfluoropolyether modified alcohol compound (8.5 g) of the average composition: $CF_3CF_2CF_2O(CF_2CF_2CF_2O)_{20}CF_2CF_2CH_2OH$, 1,3-bis(trifluoromethyl)benzene (45 g) and KOH (0.33 g) were added and stirred at 70° C. Then, pentaerythritol triallyl ether bromo adduct (A) (3.10 g) obtained in Synthesizing Example 1 and tetrabutylammonium bromide (0.12 g) were added and stirred at 70° C., and then separated and purified to obtain perfluoropolyether group containing allyloxy compound (D) having allyl group at the terminal (4.81 g).

Perfluoropolyether group containing allyloxy compound (D):

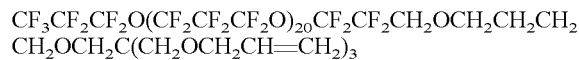

Synthesizing Example 5

To a four necked flask of 50 mL provided with a reflux condenser, a thermometer and a stirrer, perfluoropolyether group containing allyloxy compound (D) (4.5 g) obtained in Synthesizing Example 4, 1,3-bis(trifluoromethyl)benzene (8.87 g), and triacetoxysilane (0.01 g) were added and stirred for 30 minutes. Then, trichlorosilane (1.42 g) and a xylene solution (0.04 ml) containing Pt complex of 1,3-divinyl-1,1,3,3-tetramethyldisiloxane at 2% were added and stirred at 60° C. for 3 hours. Then, volatile content was distilled off under a reduced pressure to obtain, and a mixture of methanol (0.16 g) and trimethyl orthoformate (6.44 g) was added, and then, stirred at 50° C. and separate and purified to obtain perfluoropolyether group containing silane compound (E) having trimethoxysilyl group at the terminal (4.36 g).

perfluoropolyether group containing silane compound (E):

$CF_3CF_2CF_2O(CF_2CF_2CF_2O)_{20}CF_2CF_2CH_2OCH_2CH_2CH_2CH_2OCH_2C(CH_2OCH_2CH_2CH_2Si(OMe)_3)_3$

Synthesizing Example 6

To a four necked flask of 50 mL provided with a reflux condenser, a thermometer and a stirrer, perfluoropolyether group containing allyloxy compound of $CF_3O(CF_2CF_2O)_{20}(CF_2O)_{16}CF_2C(OCH_2CH=CH_2)(CH_2CH=CH_2)_2$ (5.0 g) (with proviso that although the compound comprising a small amount of the repeating units $(CF_2CF_2CF_2CF_2O)$ and/or $(CF_2CF_2CF_2O)$ in the mixture, it was not taken into consideration since it was a very small amount), 1,3-bis(trifluoromethyl)benzene (9.0 g), and triacetoxysilane (0.01 g) were added and stirred for 30 minutes. Then, trichlorosilane (1.50 g) and a xylene solution (0.05 ml) containing Pt complex of 1,3-divinyl-1,1,3,3-tetramethyldisiloxane at 2% were added and stirred at 60° C. for 3 hours. Then, volatile content was distilled off under a reduced pressure to obtain, and a mixture of methanol (0.20 g) and trimethyl orthoformate (7.0 g) was added, and then, stirred at 50° C. and separate and purified to obtain perfluoropolyether group containing silane compound (F) having trimethoxysilyl group at the terminal (5.32 g).

Perfluoropolyether group containing silane compound (F):

$CF_3O(CF_2CF_2O)_{20}(CF_2O)_{16}CF_2C[OCH_2CH_2CH_2Si(OMe)_3][CH_2CH_2CH_2Si(OMe)_3]_2$

Synthesizing Example 7

To a four necked flask of 50 mL provided with a reflux condenser, a thermometer and a stirrer, perfluoropolyether group containing allyloxy compound of $CF_3CF_2CF_2O(CF_2CF_2CF_2O)_{20}CF_2CF_2C(OCH_2CH=CH_2)(CH_2CH=CH_2)_2$ (4.0 g), 1,3-bis(trifluoromethyl)benzene (7.2 g), and triacetoxysilane (0.01 g) were added and stirred for 30 minutes. Then, trichlorosilane (1.20 g) and a xylene solution (0.04 ml) containing Pt complex of 1,3-divinyl-1,1,3,3-tetramethyldisiloxane at 2% were added and stirred at 60° C. for 3 hours. Then, volatile content was distilled off under a reduced pressure to obtain, and a mixture of methanol (0.16 g) and trimethyl orthoformate (5.6 g) was added, and then, stirred at 50° C. and separate and purified to obtain perfluoropolyether group containing silane compound (G) having trimethoxysilyl group at the terminal (4.4 g).

Perfluoropolyether group containing silane compound (G):

$CF_3CF_2CF_2O(CF_2CF_2CF_2O)_{20}CF_2CF_2C[OCH_2CH_2CH_2Si(OMe)_3][CH_2CH_2CH_2Si(OMe)_3]_2$

Example 1

Compound (C) obtained in Synthesizing Example 3 was dissolved in hydrofluoroether (Novec HFE7200 manufactured by Sumitomo 3M Ltd.)) such that the concentration was 20 wt % to prepare Surface-treating agent 1.

Surface-treating agent 1 prepared in the above was vacuum deposited on a chemical strengthening glass (Gorilla glass manufactured by Corning Incorporated; thickness: 0.7 mm). Processing condition of the vacuum deposition was a pressure of $3.0 \times 10^{-3}$ Pa. Firstly, silicon dioxide was deposited on the surface of this chemical strengthening glass in a manner of an electron-beam deposition. Subsequently, the surface-treating agent of 2 mg (that is, it contained of 0.4 mg of Compound (C)) was vacuum-deposited per one plate of the chemical strengthening glass (55 mm×100 mm). Then, the chemical strengthening glass having the deposited layer was stood under a temperature of 20° C. and a humidity of 65% for 24 hours.

Example 2

The surface-treating agent was prepared and the surface-treating layer was formed similarly to Example 1 except that Compound (E) obtained in Synthesis Example 5 was used in place of Compound (C).

Example 3

The surface-treating agent was prepared and the surface-treating layer was formed similarly to Example 1 except that Compound (F) obtained in Synthesis Example 6 was used in place of Compound (C).

Example 4

The surface-treating agent was prepared and the surface-treating layer was formed similarly to Example 1 except that Compound (G) obtained in Synthesis Example 7 was used in place of Compound (C).

Example 5

The surface-treating agent was prepared and the surface-treating layer was formed similarly to Example 1 except that perfluoropolyether group containing silane compound (H) shown below was used in place of Compound (C).

Perfluoropolyether group containing silane compound (H):

$CF_3O(CF_2CF_2O)_{20}(CF_2O)_{16}CF_2C[OC(O)NHCH_2CH_2CH_2Si(OMe)_3][CH_2CH_2CH_2Si(OMe)_3]_2$

Comparative Examples 1-3

The surface-treating agent was prepared and the surface-treating layer was formed similarly to Example 1 except that Control compounds 1-3 shown below were used in place of Compound (C).

Control compund 1

$CF_3O(CF_2CF_2O)_{20}(CF_2O)_{16}CF_2CH_2OCH_2CH_2CH_2Si(OCH_3)_3$

Control compound 2

$CF_3O(CF_2CF_2O)_{20}(CF_2O)_{16}CF_2CH_2OCF_2CFHOCF_2CF_2-(CH_2CH)_g-H$
                                                                                    |
                                                                              $Si(OCH_3)_3$ wherein g is an integer of 1-6.

Control compound 3

$$CF_3CF_2CF_2O(CF_2CF_2CF_2O)_{20}CF_2CF_2-(CH_2CH)_g-H$$
$$|$$
$$Si(OCH_3)_3$$

wherein g is an integer of 1-6.

Evaluation of Friction Durability

A static water contact angle of the surface-treating layers formed on the surface of the base material in the above Examples and Comparative Examples respectively was measured. The static water contact angle was measured for 1 µL of water by using a contact angle measuring instrument (manufactured by KYOWA INTERFACE SCIENCE Co., Ltd.).

Firstly, as an initial evaluation, the static water contact angle of the surface-treating layer of which the surface had not still contacted with anything after formation thereof was measured (the number of rubbing is zero). Then, as an evaluation of the friction durability, a steel wool friction durability evaluation was performed. Specifically, the base material on which the surface-treating layer was formed was horizontally arranged, and then, a steel wool (grade No. 0000, 5 mm×10 mm×10 mm) was contacted with the exposed surface of the surface-treating layer and a load of 1000 gf was applied thereon. Then, the steel wool was shuttled at a rate of 140 mm/second while applying the load. The static water contact angle (degree) was measured per 2,500 shuttling. The evaluation was stopped when the measured value of the contact angle became to be less than 100 degree. The results are shown in Table 1 (in the table, the symbol "-" represents no measurement).

TABLE 1

| Number of rubbing (times) | Contact Angle (degree) | | | | |
|---|---|---|---|---|---|
| | Example 1 | Example 2 | Example 3 | Example 4 | Example 5 |
| 0 | 113.1 | 113.8 | 113.4 | 113.0 | 113.2 |
| 2500 | 112.7 | 112.5 | 112.1 | 111.9 | 111.7 |
| 5000 | 112.3 | 111.4 | 112.0 | 109.5 | 108.8 |
| 7500 | 112.0 | 111.2 | 110.6 | 109.2 | 108.4 |
| 10000 | 112.3 | 108.2 | 107.1 | 107.5 | 107.4 |
| 12500 | 112.2 | 106.4 | 105.9 | 106.2 | 104.2 |
| 15000 | 111.1 | 106.1 | 104.7 | 104.0 | 103.8 |
| 17500 | 110.9 | 104.9 | 104.8 | 103.7 | 103.5 |
| 20000 | 109.6 | 104.5 | 103.9 | 102.6 | 102.4 |
| 22500 | 108.3 | 102.7 | 102.4 | 102.2 | 101.9 |

| Number of rubbing (times) | Contact Angle (degree) | | |
|---|---|---|---|
| | Comparative Example 1 | Comparative Example 2 | Comparative Example 3 |
| 0 | 113.0 | 112.8 | 113.6 |
| 2500 | 104.0 | 110.9 | 108.2 |
| 5000 | 74.3 | 110.4 | 92.5 |
| 7500 | — | 107.2 | — |
| 10000 | — | 105.5 | — |
| 12500 | — | 104.2 | — |
| 15000 | — | 95.0 | — |
| 17500 | — | — | — |
| 20000 | — | — | — |
| 22500 | — | — | — |

As understood from the above results, it was confirmed that Examples 1-5 using the perfluoropolyether group containing silane compound of the present invention having some Si(OMe)₃ branching from a carbon atom of the main chain showed improved friction durability in comparison with Comparative Examples 1-3 using the compounds having no such structure.

INDUSTRIAL APPLICABILITY

The present invention is suitably applied for forming a surface-treating layer on a surface of various base materials, in particular, an optical member in which transparency is required.

The invention claimed is:

1. A perfluoro(poly)ether group containing silane compound of formula (1a):

$$Rf\text{-PFPE})\text{-}X\text{—}C(\text{—}Y\text{—}SiR^5_nR^6_{3-n})_3 \quad (1a)$$

wherein:

Rf is each independently at each occurrence an alkyl group having 1-16 carbon atoms which may be substituted by one or more fluorine atoms;

PFPE is each independently at each occurrence a group of the formula:

$$-(OC_4F_8)_a-(OC_3F_6)_b-(OC_2F_4)_c-(OCF_2)_d-$$

wherein a, b, c and d are each independently an integer of 0-200, the sum of a, b, c and d is 5 or more, and the occurrence order of the respective repeating units in parentheses with the subscript a, b, c or d is not limited in the formula;

PFPE binds to Rf via oxygen atom at its left end and binds to X via carbon atom at its right end in formula (1a);

X is each independently the following divalent organic group;

a $C_{1-20}$ alkylene group,

—$R^{31}$—$X^c$—$R^{31}$—, or wherein $R^{31}$ is each independently a single bond, or —(CH$_2$)$_{s'}$— (wherein s' is an integer of 1-20), with the proviso that at least one of $R^{31}$ is not a single bond;

$X^c$ is

—O—,

—CONR$^{34}$—, or

—O—CONR$^{34}$—, wherein $R^{34}$ is each independently at each occurrence a hydrogen atom or a $C_{1-6}$ alkyl group;

Y is each independently at each occurrence a $C_{1-6}$ alkylene group, —(CH$_2$)$_{g'}$—O—(CH$_2$)$_{h'}$— (wherein g' is an integer of 0-6, and h' is an integer of 0-6), or -phenylene-(CH$_2$)$_{i'}$— (wherein i' is an integer of 0-6);

$R^5$ is each independently at each occurrence a hydroxyl group or —OR, —OCOR, —O—N=C(R)$_2$, —N(R)$_2$, —NHR, halogen (wherein R is a substituted or non-substituted alkyl group having 1-4 carbon atoms);

$R^6$ is each independently at each occurrence a hydrogen atom or a lower alkyl group;

n is an integer of 1-3 independently per unit —Y—SiR$^5_n$R$^6_{3-n}$.

2. The perfluoro(poly)ether group containing silane compound according to claim 1 wherein Rf is a perfluoroalkyl group having 1-16 carbon atoms.

3. The perfluoro(poly)ether group containing silane compound according to claim 1 wherein PFPE is a group of any of the following formulae (i) to (iv):

$$-(OCF_2CF_2CF_2)_b- \quad (i)$$

wherein b is an integer of 1-200;

$$-(OCF(CF_3)CF_2)_b- \quad (ii)$$

wherein b is an integer of 1-200;

$$-(OCF_2CF_2CF_2CF_2)_a-(OCF_2CF_2CF_2)_b-(OCF_2CF_2)_c-(OCF_2)_d- \quad (iii)$$

wherein a and b are each independently an integer of 0-30, c and d are each independently an integer of 1-200, the sum of a, b, c and d is 5 or more, and the occurrence order of the respective repeating units in parentheses with the subscript a, b, c or d is not limited in the formula; or $$-(OC_2F_4-R^8)_{n''}- \quad (iv)$$

wherein $R^8$ is a group selected from $OC_2F_4$, $OC_3F_6$ and $OC_4F_8$, or a combination of 2 or 3 groups independently selected from these groups, and the sum of $OC_2F_4$, $OC_3F_6$ and $OC_4F_8$ is 5 or more; and n" is an integer of 2-100.

4. The perfluoro(poly)ether group containing silane compound according to claim 1 wherein X is each independently selected from the group consisting of:

—CH$_2$O(CH$_2$)$_2$—,
—CH$_2$O(CH$_2$)$_3$—,
—CH$_2$O(CH$_2$)$_6$—,
—(CH$_2$)$_2$—,
—(CH$_2$)$_3$—,
—(CH$_2$)$_4$—,
—(CH$_2$)$_5$—,
—(CH$_2$)$_6$—,
—CONH—(CH$_2$)$_3$—,
—CON(CH$_3$)—(CH$_2$)$_3$—,
—CONH—(CH$_2$)$_6$—,
—CON(CH$_3$)—(CH$_2$)$_6$—,
—CH$_2$O—CONH—(CH$_2$)$_3$—, and
—CH$_2$O—CONH—(CH$_2$)$_6$—.

5. The perfluoro(poly)ether group containing silane compound according to claim 1 wherein an average molecular weight of the Rf-PFPE moiety is 500-30,000.

6. The perfluoro(poly)ether group containing silane compound according to claim 1 having an average molecular weight of 2,000-32,000.

7. A surface-treating agent comprising at least one perfluoro(poly)ether group containing silane compound of the formula (1a) according to claim 1.

8. The surface-treating agent according to claim 7 further comprising one or more components selected form a fluorine-containing oil, a silicone oil and a catalyst.

9. The surface-treating agent according to claim 8 wherein the fluorine-containing oil is one or more compounds of the formula (3):

$$R^{21}-(OC_4F_8)_{a'}-(OC_3F_6)_{b'}-(OC_2F_4)_{c'}-(OCF_2)_{d'}-R^{22} \quad (3)$$

wherein:
R$^{21}$ is an alkyl group having 1-16 carbon atoms which may be substituted by one or more fluorine atoms;
R$^{22}$ is an alkyl group having 1-16 carbon atoms which may be substituted by one or more fluorine atoms, a fluorine atom or a hydrogen atom; and a', b', c' and d' are the repeating number of each of four repeating units of perfluoro(poly)ether which constitutes a main backbone of the polymer, and are each independently an integer of 0 or more and 300 or less, the sum of a', b', c' and d' is 1 or more, and the occurrence order of the respective repeating units in parentheses with the subscript a', b', c' and d' is not limited in the formula.

10. The surface-treating agent according to claim 8 wherein the fluorine-containing oil is one or more compounds of the formula (3a) or (3b):

$$R^{21}-(OCF_2CF_2CF_2)_{b''}-R^{22} \quad (3a)$$

$$R^{21}-(OCF_2CF_2CF_2CF_2)_{a''}-(OCF_2CF_2CF_2)_{b''}-(OCF_2CF_2)_{c''}-(OCF_2)_{d''}-R^{22} \quad (3b)$$

wherein:
R$^{21}$ is an alkyl group having 1-16 carbon atoms which may be substituted by one or more fluorine atoms;
R$^{22}$ is an alkyl group having 1-16 carbon atoms which may be substituted by one or more fluorine atoms, a fluorine atom or a hydrogen atom;
in the formula (3a), b" is an integer of 1 or more and 100 or less;
in the formula (3b), a" and b" are each independently an integer of 0 or more and 30 or less, and c" and d" are each independently an integer of 1 or more and 300 or less; and
the occurrence order of the respective repeating units in parentheses with the subscript a", b", c" or d" is not limited in the formula.

11. The surface-treating agent according to claim 10 comprising at least one compound of the formula (3b).

12. The surface-treating agent according to claim 10 wherein a mass ratio of the perfluoro(poly)ether group containing silane compound of the formula (1a) and the compound of the formula (3b) is 4:1-1:4.

13. The surface-treating agent according to claim 10 wherein the compound of the formula (3a) has a number average molecular weight of 2,000-8,000.

14. The surface-treating agent according to claim 10 wherein the compound of the formula (3b) has a number average molecular weight of 2,000-30,000.

15. The surface-treating agent according to claim 10 wherein the compound of the formula (3b) has a number average molecular weight of 8,000-30,000.

16. The surface-treating agent according to claim 7 further comprising a solvent.

17. The surface-treating agent according to claim 7 which is used as an antifouling-coating agent or a water-proof coating agent.

18. The surface-treating agent according to claim 7 for vacuum deposition.

19. A pellet containing the surface-treating agent according to claim 7.

20. An article comprising a base material and a layer which is formed on a surface of the base material from the surface treating agent according to claim 7.

21. An article comprising a base material and a layer which is formed on a surface of the base material from the compound according to claim 1.

22. The article according to claim 21 wherein the article is an optical member.

23. The article according to claim 21 wherein the article is a display.

* * * * *